United States Patent
Scarsella et al.

(10) Patent No.: US 11,231,491 B2
(45) Date of Patent: Jan. 25, 2022

(54) ROBUST ULTRASOUND TRANSDUCER PROBES HAVING PROTECTED INTEGRATED CIRCUIT INTERCONNECTS

(71) Applicant: KONINKLIJKE PHILIPS N.V., Eindhoven (NL)

(72) Inventors: Michael Scarsella, Eindhoven (NL); Wojtek Sudol, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 161 days.

(21) Appl. No.: 15/034,082

(22) PCT Filed: Oct. 29, 2014

(86) PCT No.: PCT/IB2014/065675
§ 371 (c)(1),
(2) Date: May 3, 2016

(87) PCT Pub. No.: WO2015/068080
PCT Pub. Date: May 14, 2015

(65) Prior Publication Data
US 2016/0282455 A1    Sep. 29, 2016

Related U.S. Application Data

(60) Provisional application No. 61/902,313, filed on Nov. 11, 2013.

(51) Int. Cl.
*G01S 7/52*    (2006.01)
*A61B 8/00*    (2006.01)
(Continued)

(52) U.S. Cl.
CPC .......... *G01S 7/5208* (2013.01); *A61B 8/4444* (2013.01); *A61B 8/4494* (2013.01);
(Continued)

(58) Field of Classification Search
CPC .......... G01S 7/52; G01S 15/89; G01S 7/5208; G01S 15/8925; G01S 15/8915;
(Continued)

(56) References Cited

U.S. PATENT DOCUMENTS 3,276,535 A * 10/1966 Shaw ...................... H04R 1/342
                                                        181/158
5,493,541 A *  2/1996 Snyder .................. B06B 1/0622
                                                        310/334
(Continued)

FOREIGN PATENT DOCUMENTS

WO    2005055195 A1    6/2005
WO    2006018805 A1    2/2006
(Continued)

*Primary Examiner* — Isam A Alsomiri
*Assistant Examiner* — Amie M Ndure

(57) ABSTRACT

An ultrasound probe is formed with protected interconnects, thereby resulting in a more robust probe. The interconnects are mounted between an array of transducer elements and an integrated circuit. The array of transducer elements are coupled to the interconnect via flip chip bumps or other structures. Underfill material fixedly positions the interconnects to the integrated circuit. A method of making the transducer assembly is provided.

11 Claims, 5 Drawing Sheets

(51) Int. Cl.
*B06B 1/06* (2006.01)
*G01S 15/89* (2006.01)

(52) U.S. Cl.
CPC .......... *B06B 1/064* (2013.01); *G01S 15/8925*
(2013.01); *A61B 8/4488* (2013.01); *B06B 2201/55* (2013.01); *B06B 2201/76* (2013.01); *G01S 15/8915* (2013.01)

(58) Field of Classification Search
CPC ....... A61B 8/00; A61B 8/4444; A61B 8/4494; A61B 8/4488; B06B 1/06; B06B 1/064; B06B 2201/55; B06B 2201/76
See application file for complete search history.

(56) References Cited

U.S. PATENT DOCUMENTS

| | | | |
|---|---|---|---|
| 6,589,180 | B2 | 7/2003 | Erikson et al. |
| 7,309,948 | B2 | 12/2007 | Kuniyasu et al. |
| 7,451,651 | B2 | 11/2008 | Wiychik et al. |
| 9,237,880 | B2 | 1/2016 | Davidsen et al. |
| 9,510,806 | B2* | 12/2016 | Smith ................. G01S 7/52079 |
| 9,572,549 | B2* | 2/2017 | Belevich ................ A61B 6/584 |
| 9,883,848 | B2* | 2/2018 | Specht ................ G01S 15/8913 |
| 2002/0156373 | A1* | 10/2002 | Wakabayashi ........ B06B 1/0622 600/437 |
| 2003/0170932 | A1 | 9/2003 | Bolken |
| 2007/0157732 | A1* | 7/2007 | Lee ........................ B06B 1/0629 73/634 |
| 2008/0106976 | A1* | 5/2008 | Davidsen .............. B06B 1/0622 367/140 |
| 2010/0168581 | A1* | 7/2010 | Knowles ................ G10K 11/02 600/459 |
| 2010/0251718 | A1* | 10/2010 | Ito .......................... F01D 25/04 60/725 |
| 2011/0220433 | A1* | 9/2011 | Nakamura .............. F01D 9/023 181/213 |
| 2012/0081994 | A1* | 4/2012 | Husom .................. G01V 1/201 367/16 |
| 2012/0238880 | A1* | 9/2012 | Davidsen .............. B06B 1/0629 600/459 |
| 2013/0261449 | A1* | 10/2013 | Tashiro ................ A61B 8/0891 600/437 |
| 2014/0187960 | A1* | 7/2014 | Corl |
| 2020/0003896 | A1* | 1/2020 | Call ........................ G01S 15/89 |

FOREIGN PATENT DOCUMENTS

| | | |
|---|---|---|
| WO | 2012085724 A1 | 6/2012 |
| WO | 2013148515 A2 | 10/2013 |

* cited by examiner

ROBUST ULTRASOUND TRANSDUCER PROBES HAVING PROTECTED INTEGRATED CIRCUIT INTERCONNECTS This application is the U.S. National Phase application under 35 U.S.C. § 371 of International Application No. PCT/IB2014/065675, filed on Oct. 29, 2014, which claims the benefit of U.S. Provisional Application No. 61/902,313 filed Nov. 11, 2013. These applications are hereby incorporated by reference herein.

This invention relates to medical diagnostic ultrasound systems and, in particular, to mounting of interconnects in an ultrasonic transducer array stack.

Two dimensional array transducers are used in ultrasonic imaging to electronically scan in three dimensions. Two dimensional arrays have numerous rows and columns of transducer elements in both the azimuth and elevation directions, which would require a large number of cable conductors to couple signals between the many elements of the probe and the mainframe ultrasound system. A preferred technique for minimizing the number of signal conductors in the probe cable is to perform at least some of the beamforming in the probe in a microbeamformer ASIC (application specific integrated circuit.) This technique requires only a relatively few number of partially beamformed signals to be coupled to the mainframe ultrasound system, thereby reducing the required number of signal conductors in the cable. However a large number of signal connections must be made between the two dimensional array and the microbeamformer ASIC, one for each element of the array. An efficient way to make these connections is to design the transducer array and the ASIC to have flip-chip interconnections, whereby electrode pads of the transducer array are bump bonded directly to corresponding conductive pads of the ASIC. In one type of two-dimensional ultrasound transducer design, all transducer elements of an array are attached and individually electrically connected to a surface of an integrated circuit (IC) via "flip-chip" technology using conductive bumps. This microbeamformer IC provides electrical control of the elements, such as for beam forming, signal amplification, etc., and provides the means of interfacing the thousands of array elements to the mainframe beamformer of the ultrasound system.

One example of a known design of an ultrasound transducer is illustrated in FIG. 1. The ultrasound transducer 10 includes a flat array of acoustic elements 12 that are coupled to a surface of an integrated circuit 14 via flip-chip conductive bumps 16. A flip-chip underfill material 18 is included within a region between the integrated circuit 14 and the flat array of acoustic elements 12, surrounding the flip-chip conductive bumps 16. Transducer 10 further includes a transducer base 20 and an interconnection cable 22. Interconnection cable 22 connects the integrated circuit 14 and an external cable (not shown). Integrated circuit 14 is electrically coupled to the interconnection cable 22 using interconnects such as wire bonds 24.

Interconnects, such as the wire bonds 24, are used to transmit power and signals to and from the integrated circuit. Unfortunately, the interconnects are close to the lens of the transducer, thereby making them susceptible to damage, intermittency, and/or disconnection. Some approaches have been used to reduce these problems that include staking the wire bonds to the integrated circuit using an adhesive drop that hardened over the interconnect. However, the staking increases complexity of the fabrication process. Other techniques that do not use staking include positioning a covering structure extending from the top of the acoustic stack and over the interconnects. Problematically, the covering structure can bend and become weak over time.

There is a need for improved structures and methods for reliably protecting interconnects during fabrication and use of ultrasound transducers.

In accordance with the principles of the present invention, an ultrasound probe is provided with protected interconnects. The interconnects are mounted between an array of transducer elements and an integrated circuit for the transducer elements, with the overhang of the acoustic stack above the connection point protecting the interconnect. Underfill material fixedly positions the interconnects relative to the integrated circuit. These features result in a more robust probe structure.

Figure 8:
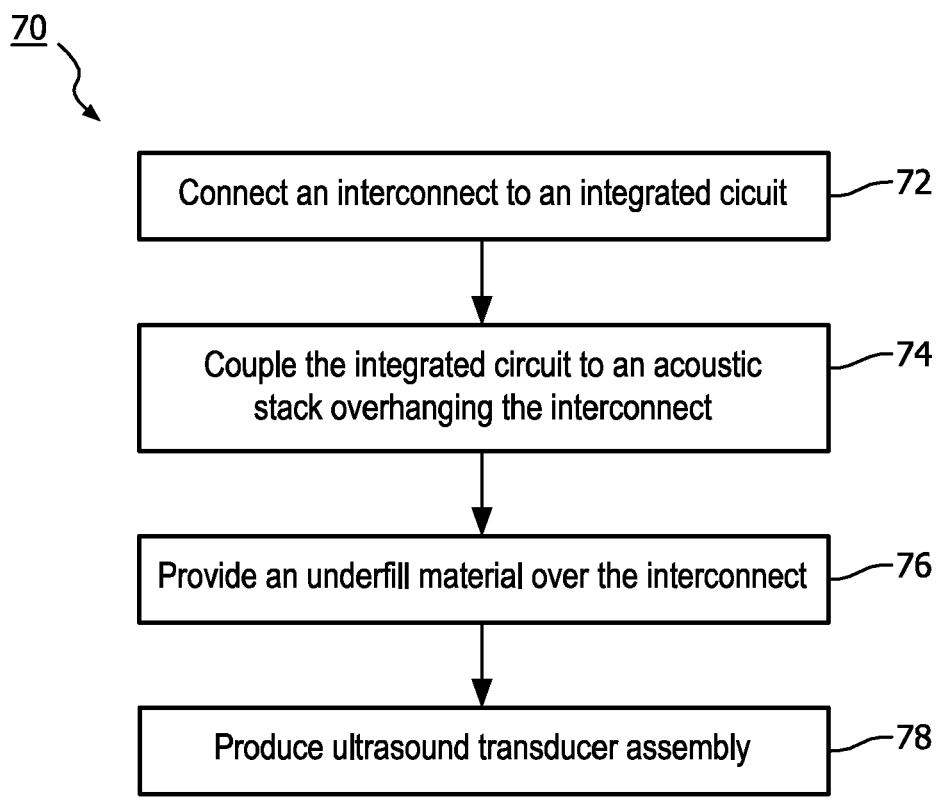

FIG. 8 provides a method of making protected interconnects in a transducer assembly in accordance with the principles of the present invention.

An implementation of the present invention includes an ultrasonic transducer array assembly having an array of transducer elements. The transducer elements include a plurality of layers. The layers include a piezoelectric layer, such as lead zirconium titanate (PZT), and matching layers that match the acoustic impedance of the piezoelectric layer to that of the probe lens and the body being imaged. A metallized layer is included to electrically couple the piezoelectric layer to an integrated circuit in the assembly. Other layers can also be included according to desired characteristics for the transducer array. The integrated circuit is coupled to the array of transducer elements. Coupling of the integrated circuit can be carried out using flip-chip techniques, or any other suitable technique that provides the necessary electrical coupling between the integrated circuit and the transducer elements. As will be described further below, interconnects are positioned in contact with the integrated circuit and fixedly positioned between the integrated circuit and at least one layer of the layers in the transducer elements in the array. The space between the integrated circuit and the layers can be tailored according to the dimensions of the interconnect. For example, additional spacing may be used if wire bonds are connected to the integrated circuit. The wire bonds include a bend height that can provide the need for increased height between the surface of the integrated circuit and a layer in the acoustic stack above the point of interconnection. As compared to a wire bond, a flex circuit provides a profile having a lower height, and thus uses less spacing when it is laid down over the surface of the integrated circuit. Furthermore, having the interconnect positioned within the space between the transducer elements and the integrated circuit provides for more robust transducers, since the interconnect connection to the integrated circuit is protected from damage and/or disconnection.

Figure 1:
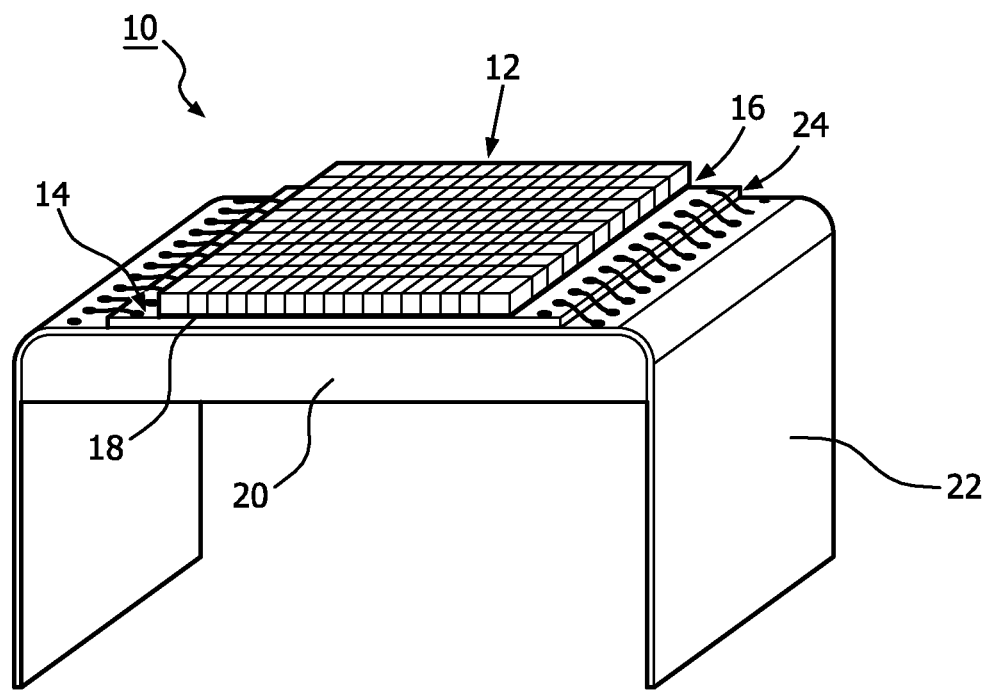
FIG. 1 is a perspective view of a conventional ultrasound sensor.
Figure 2:
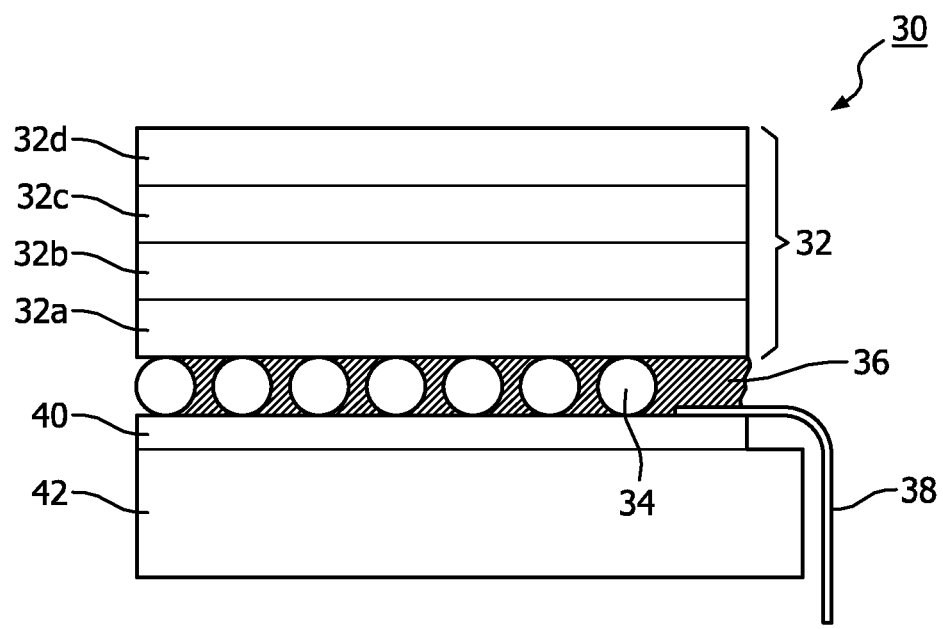
FIG. 2 illustrates an acoustic stack constructed in accordance with the principles of the present invention.

FIG. 2 schematically shows an acoustic stack 30 with a protected interconnect constructed in accordance with the principles of the present invention. The acoustic stack includes a plurality of layers 32, such as a metallized layer 32a, a piezoelectric layer 32b such as PZT, and two acoustic matching layers 32c and 32d bonded to the piezoelectric layer 32b. The matching layers match the acoustic impedance of the piezoelectric material to that of the body being diagnosed, generally in steps of progressive changes in the acoustic impedance of each matching layer. The integrated circuit 40, which is bonded to a backing block 42, is coupled to the metallized layer 32a by stud bumps 34. The interconnect 38, which is shown as a flex circuit, contacts one or more conductors of the integrated circuit 40 and is fixedly held in that position with an underfill layer 36. The underfill layer can include an electroinsulating material, such as epoxy resin.

The arrangement of the interconnect between the integrated circuit and the acoustic stack provides several benefits. For example, the interconnect (e.g., flex circuits or wire bonds) are held rigidly in place such that less damage and fewer disconnects result from use of the probe. In addition, a flexible circuit can be coupled to the integrated circuit, held in place by underfill material, and then bent to any particular angle that is needed for proper electrical connection in the probe. With "staking" solutions as described above, the bending of the flexible circuit often leads to displacement of the adhesive and thus disconnection of the interconnect. The present invention overcomes this problem by holding the interconnect rigidly during bending. Additionally, space savings are also realized because the interconnect can extend further toward the center of the integrated circuit, thereby taking less space in the lateral dimension of the transducer probe. More efficient spacing is also realized in the vertical dimension, thereby leaving more room between the top of the acoustic stack and the probe lens.

In addition to fixedly holding the interconnect on the integrated circuit, the underfill provides various other functions. It acts to hold the integrated circuit and the acoustic stack together since the connection of the bumps alone may not be adequate for the strength of the assembly. In some embodiments, the flip-chip variations require a good hermetic seal of the joint that the underfill can provide. In addition, after the flip-chip connection is completed, a dicing process is done to separate the acoustic stack into individual elements. The separating cut needs to be deeper than the last layer of the acoustic stack, but not too deep so as to reach the IC. The underfill supports each individual acoustic element.

Figure 3:
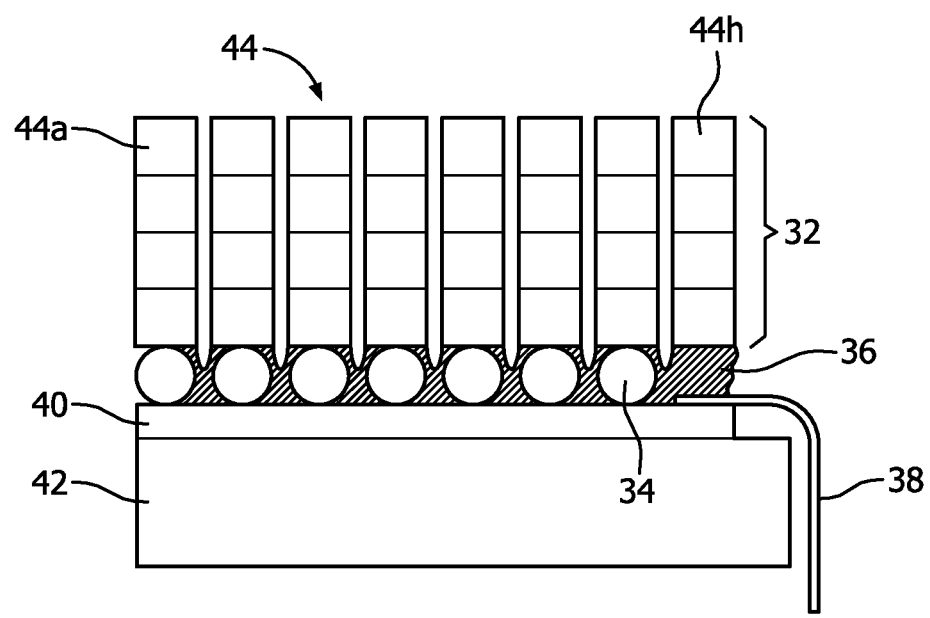
FIG. 3 illustrates diced acoustic elements in the acoustic stack of FIG. 2.

As shown in FIG. 3, the acoustic stack 30 of FIG. 2 is diced by dicing cuts to form an array 44 of individual transducer elements 44a, eight of which are shown in this example. The array 44 can include a single row of transducer elements (a 1-D array) or be diced in two orthogonal directions to form a two-dimensional (2D) matrix array of transducer elements. The integrated circuit 40, an ASIC, provides transmit signals for the transducer elements 44a and receives and processes signals from the elements. Conductive pads on the upper surface of the integrated circuit 40 are electrically coupled to conductive pads on the bottoms of the transducer elements by stud bumps 34, which may be formed of solder or conductive epoxy. Signals are provided to and from the integrated circuit 40 by connections to the flex circuit 38. Below the integrated circuit 40 is a backing block 42, which attenuates acoustic energy emanating from the bottom of the transducer stack and conducts heat generated by the integrated circuit away from the integrated circuit and the transducer stack and away from the patient-contacting end of the transducer probe. A variety of backing blocks can be used, including a backing block including a porous foam material filled with resin as disclosed in WO2012/123908 to Sudol et al., which is incorporated by reference herein. It is seen in FIGS. 2 and 3 that end element 44h in this implementation is not an acoustically functioning transducer element and is not connected to the integrated circuit by a stud bump. That is because this dummy end element serves the protection function of the present invention, overhanging the attachment point of the interconnect 38 to the integrated circuit and solidifying the connection with the underfill material between the dummy end element 44h and the integrated circuit.

Figure 4:
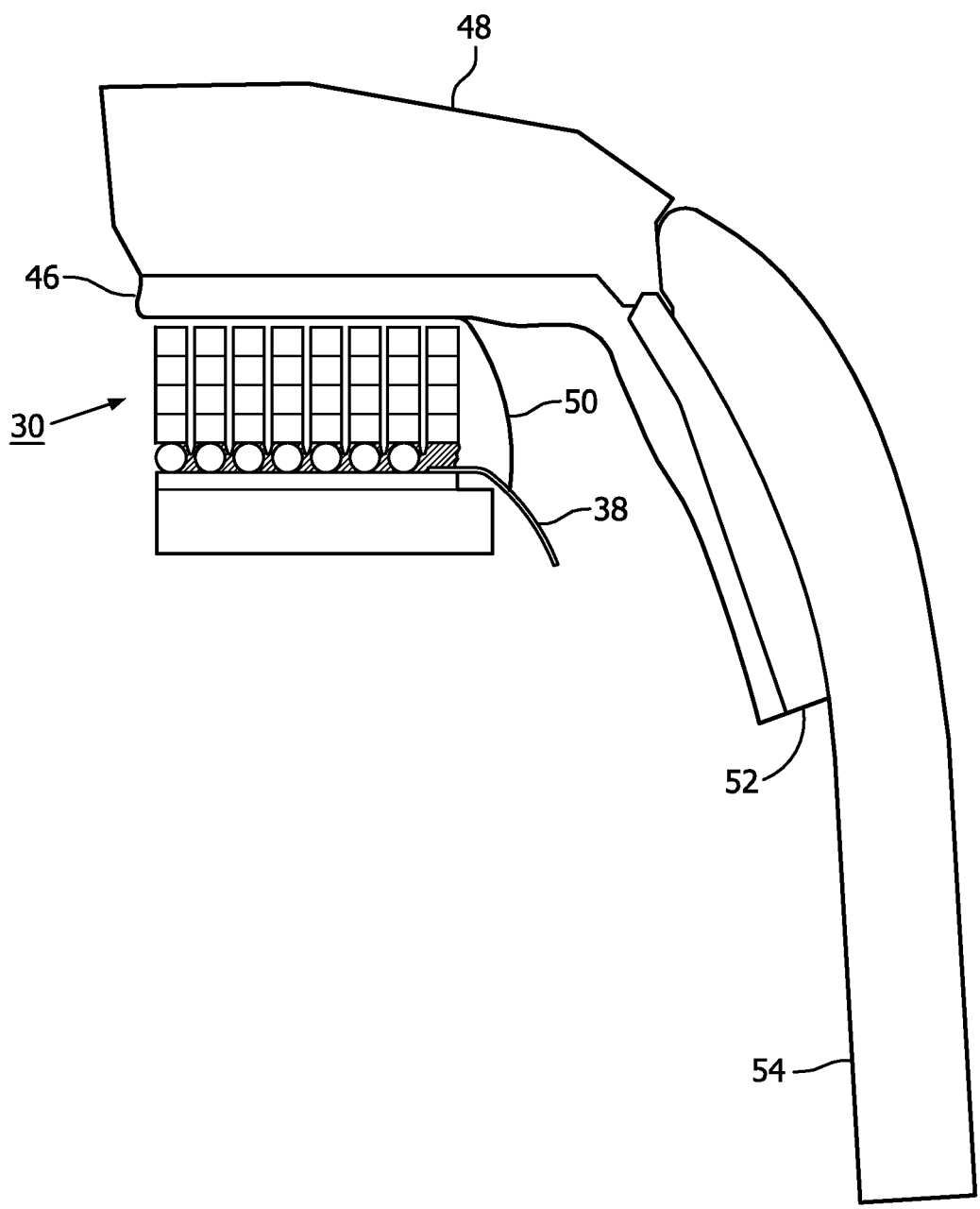
FIG. 4 illustrates the acoustic stack of FIG. 2 when assembled in a transducer probe with a lens cover.

FIG. 4 illustrates the transducer stack assembly of FIG. 3 when assembled inside a transducer probe. In the probe, the matching layer 32d in the acoustic stack 30 is bonded to the acoustic lens 48. Ultrasound waves are transmitted through the lens 48 and into the patient's body during imaging, and echoes received in response to these waves are received by the transducer stack through the lens 48. In an alternative embodiment, the acoustic lens 48 is replaced with a window, i.e., an element with no focusing acoustical power. The window may be made of the window material PEBAX, for instance. In this embodiment, a third matching layer 46 (e.g., a low density polyethylene (LDPE) film) also serves to enclose the transducer stack as it is wrapped around the stack and bonded by an epoxy bond 52 to the probe housing 54. A ground plane 50 is bonded to the top of the second matching layer 32d, and is formed as a conductive layer on a film of the third matching layer 46. The ground plane is electrically coupled to the transducer elements through the electrically conductive matching layers and is connected to a ground conductor of flex circuit 38. Further details of this type of construction are found in US patent publication no. US 2010/0168581 (Knowles et al.), which is incorporated herein by reference.

Figure 5:
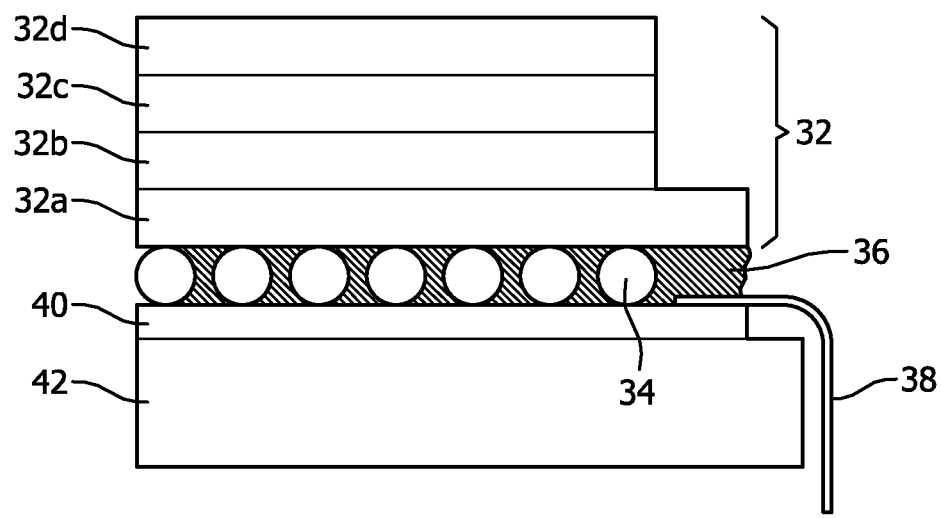
FIG. 5 is an acoustic stack having one acoustic layer covering an interconnect in accordance with the principles of the present invention.

Another example of a transducer assembly of the present invention is illustrated in FIG. 5. In this example, only one or some of the layers in the acoustic stack 30 need be extended beyond the active acoustic area over the connection of the interconnect to the integrated circuit. For example, certain layers that are more costly, such as the piezoelectric layer, may be limited to the active acoustic area thereby saving material cost of a full dummy element as used in FIG. 4. As FIG. 5 illustrates, the plurality of layers 32 can be arranged to extend at different locations over the integrated circuit. The bottom layer 32a, for example, extends to a plane that is at or about an edge of the integrated circuit. In contrast, the other layers 32b, 32c and 32d are recessed inwardly away from the edge of the integrated circuit. In some embodiments, layers 32a and 32b can extend over to the edge of the integrated circuit. Alternatively, a portion of the integrated circuit may not be covered by a layer of the acoustic stack such that the edge of the acoustic stack is located more inward towards the center of the integrated circuit. In some embodiments, an outer edge of the integrated circuit is located in approximately the same plane with an outer edge of at least one of the plurality of layers.

Figure 6:
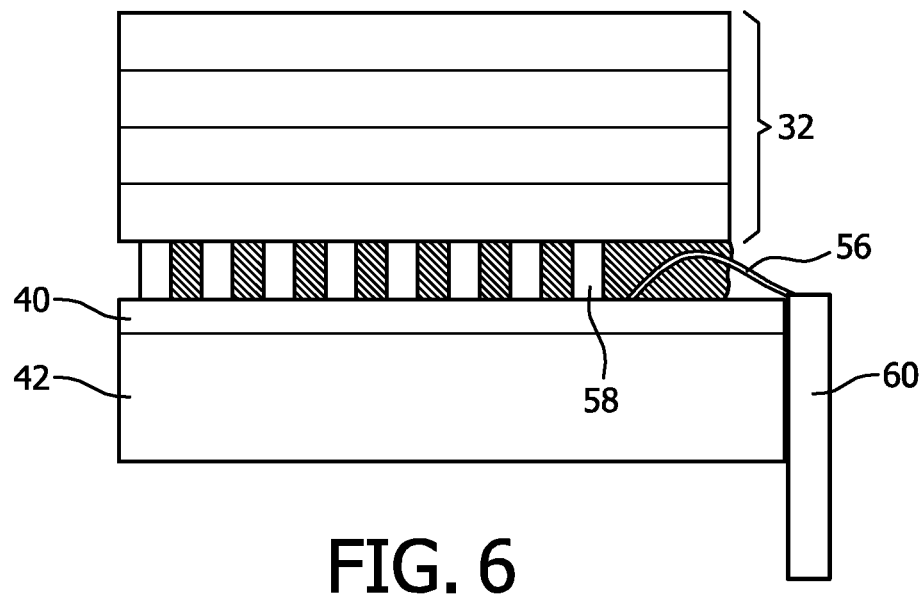
FIG. 6 illustrates an acoustic stack including a wire bond and subtractively created bumps in accordance with the principles of the present invention.

The illustrations in FIGS. 2-5 show a flexible circuit as the interconnect 38. Other types of interconnects can be used instead. FIG. 6 shows one example of using a wire bond 56 that is coupled to a flexible circuit 60 on the side of the backing block 42. Here, the wire bond 56 is coupled to a conductive pad on the surface of the integrated circuit 40 and is fixedly held in position using the underfill material 36.

Figure 7:
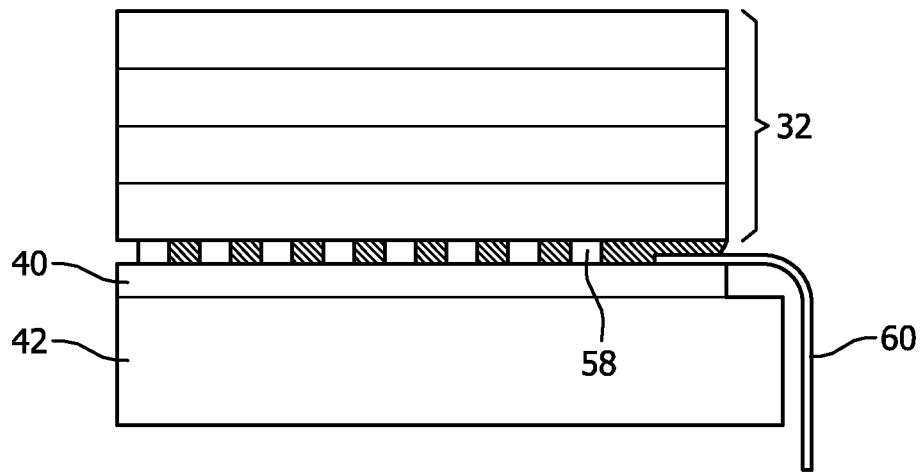
FIG. 7 illustrates an acoustic stack including a flexible circuit and subtractively created bumps in accordance with the principles of the present invention.

FIGS. 6 and 7 illustrate the use of subtractive bumps for connecting the integrated circuit 40 to the acoustic stack 32. Methods of making transducer assemblies with subtractive bumps 58 are described, e.g., in international patent publication WO2012/085724, which is incorporated herein by reference. The subtractive process determines the height of the bumps 58 and hence the spacing between the integrated circuit and the acoustic stack. As shown in FIGS. 6 and 7, the height of the spacing between the acoustic stack 32 and the integrated circuit 40 can be tailored for a particular interconnect. For example, the wire bond 56 in FIG. 6 includes a radius of curvature that requires the use of a height that can accommodate the wire bond 56. The flexible circuit 38 does not have a curvature in the vicinity of the bonding area to the integrated circuit. As such, less space is needed between the integrated circuit and the acoustic stack.

FIG. 8 describes a method of making an ultrasound transducer assembly having protected interconnects in accordance with the present invention. The method 70 includes an initial step 72 of connecting an interconnect (or interconnects) to an integrated circuit. The interconnect can be positioned to contact a conductive pad on the surface of the integrated circuit. To assist with holding the interconnect in place, a small amount of adhesive or other sticking material can be applied to the interconnect to fix it to the integrated circuit for further processing. Step 74 includes coupling the integrated circuit to an acoustic stack which is above the interconnect. This step can be done after connecting the integrated circuit to the interconnect. Alternatively, the interconnect can be inserted between the integrated circuit and the acoustic stack after the acoustic stack is coupled to the integrated circuit. An underfill material is provided in step 76 such that the underfill material covers the interconnect and fixedly holds it in position and in contact with the integrated circuit. With the interconnects protected and fixedly held in between the acoustic stack and the integrated circuit, dicing to form an array of transducer elements and additional manufacturing steps for producing the transducer assembly (Step 78) is carried out, providing improved robustness of the protected interconnect.

What is claimed is:

1. An ultrasonic transducer array assembly comprising:
    an array of transducer elements comprising a plurality of functioning transducer elements and a non-functioning transducer element, wherein the non-functioning transducer element comprises a plurality of layers that is the same as the plurality of layers of the plurality of functioning transducer elements;
    an integrated circuit comprising a first side and an opposing second side;
    an underfill material positioned between the first side of the integrated circuit and a bottom layer of the plurality of layers, the underfill material structurally coupling the array of transducer elements and the integrated circuit;
    a backing block positioned on the second side of the integrated circuit; and
    a flexible circuit electrically connected to the integrated circuit, the flexible circuit having an end structurally coupled directly to the integrated circuit, wherein the end of the flexible circuit is fixedly positioned, by the underfill material, over the first side of the integrated circuit and under the non-functioning transducer element.

2. The ultrasonic transducer array assembly of claim 1, wherein the end of the flexible circuit is positioned between the integrated circuit and all of the plurality of layers.

3. The ultrasonic transducer array assembly of claim 1, wherein the integrated circuit is structurally coupled to the array of transducer elements with stud bumps.

4. The ultrasonic transducer array assembly of claim 1, wherein the integrated circuit is structurally coupled to the array of transducer elements with subtractively created bumps.

5. The ultrasonic transducer array assembly of claim 1, wherein the backing block comprises a porous foam material filled with resin.

6. The ultrasonic transducer array assembly of claim 1, wherein an outer edge of the integrated circuit is located in approximately the same plane with an outer edge of at least one of the plurality of layers.

7. A method of making an ultrasonic transducer array assembly, the method comprising:
    structurally coupling an end of a flexible circuit directly to a first side of an integrated circuit such that the flexible circuit is electrically connected to the integrated circuit; and
    positioning an underfill material between the first side of the integrated circuit and a bottom layer of a plurality of layers such that the underfill material:
        structural couples the integrated circuit to an array of transducer elements comprising a plurality of functioning transducer elements and a non-functioning transducer element, wherein the non-functioning transducer element comprises the plurality of layers that is the same as the plurality of layers of the plurality of functioning transducer elements; and
        fixedly positions the end of the flexible circuit between the first side of the integrated circuit and under the non-functioning transducer element.

8. The method of claim 7, comprising providing a backing block positioned on an opposing second side of the integrated circuit.

9. The method of claim 7, further comprising dicing the plurality of layers to form the array of transducer elements.

10. The method of claim 7, comprising positioning an outer edge of the integrated circuit in approximately the same plane with an outer edge of at least one of the plurality of layers.

11. An apparatus, comprising:
    a medical ultrasound transducer probe configured to image a body of a patient, wherein the medical ultrasound transducer probe comprises an ultrasonic transducer array assembly, wherein the ultrasonic transducer array assembly comprises:
        an array of transducer elements comprising a plurality of functioning transducer elements and a non-functioning transducer element, wherein the non-functioning transducer element comprises a plurality of layers that is the same as the plurality of layers of the plurality of functioning transducer elements;
        an integrated circuit comprising a first side and an opposing second side;
        an underfill material positioned between the first side of the integrated circuit and a bottom layer of the plurality of layers, the underfill material structurally coupling the array of transducer elements and the integrated circuit;

a backing block positioned on the second side of the integrated circuit; and a flexible circuit electrically connected to the integrated circuit, the flexible circuit having an end structurally coupled directly to the integrated circuit, wherein the end of the flexible circuit is fixedly positioned, by the underfill material, over the first side of the integrated circuit and under the non-functioning transducer element.

* * * * *